(12) United States Patent
Wiegel et al.

(10) Patent No.: US 8,349,612 B2
(45) Date of Patent: Jan. 8, 2013

(54) GUIDED STRUCTURED TESTING KIT

(75) Inventors: Christopher Wiegel, Sunnyvale, CA (US); Colleen Csavas, Burgdorf (CH); Ulrich Porsch, Weinheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 141 days.

(21) Appl. No.: 12/946,356

(22) Filed: Nov. 15, 2010

(65) Prior Publication Data

US 2012/0122227 A1 May 17, 2012

(51) Int. Cl.
*G01N 33/66* (2006.01)
*G01N 33/48* (2006.01)
*G01N 21/77* (2006.01)

(52) U.S. Cl. ............ 436/95; 436/63; 436/149; 436/164; 436/169; 422/400; 422/420; 422/430; 422/68.1; 422/82.01; 422/82.02; 422/559; 435/14; 435/287.7; 435/810

(58) Field of Classification Search .................... 436/63, 436/95, 149, 164, 169; 422/400, 420, 430, 422/68.1, 82.01, 82.02, 82.05, 559; 435/14, 435/810, 287.7; 600/365
See application file for complete search history.

(56) References Cited

U.S. PATENT DOCUMENTS

| | | | |
|---|---|---|---|
| 6,193,873 B1 | 2/2001 | Ohara et al. | |
| 6,475,372 B1 | 11/2002 | Ohara et al. | |
| 6,558,528 B1 | 5/2003 | Matzinger | |
| 6,620,310 B1 | 9/2003 | Ohara et al. | |
| 6,716,577 B1 | 4/2004 | Yu et al. | |
| 2008/0073208 A1* | 3/2008 | Wang et al. | 204/406 |
| 2008/0177149 A1 | 7/2008 | Weinert et al. | |
| 2010/0012490 A1 | 1/2010 | Hsu | |
| 2010/0015006 A1 | 1/2010 | Hsu | |
| 2010/0041084 A1* | 2/2010 | Stephens et al. | 435/14 |
| 2010/0160757 A1 | 6/2010 | Weinert et al. | |
| 2010/0212675 A1 | 8/2010 | Walling et al. | |
| 2010/0330598 A1* | 12/2010 | Thukral et al. | 435/14 |
| 2010/0331650 A1 | 12/2010 | Batman et al. | |
| 2010/0331651 A1* | 12/2010 | Groll | 600/365 |
| 2012/0094370 A1* | 4/2012 | Ramey et al. | 435/288.7 |

FOREIGN PATENT DOCUMENTS

| | | |
|---|---|---|
| EP | 1 369 688 A2 | 6/2003 |
| EP | 2 067 865 A1 | 6/2009 |
| EP | 2 218 393 A1 | 2/2010 |
| WO | 2009/155339 A1 | 12/2009 |

* cited by examiner

*Primary Examiner* — Maureen Wallenhorst
(74) *Attorney, Agent, or Firm* — Dinsmore & Shohl LLP

(57) ABSTRACT

A guided structured testing kit which may include a test strip container, a test strip meter, a testing protocol advisor, and at least one of diagnostic test strip is presented. The diagnostic test strip includes a support element, a glucose reagent provided on the support element, and a glycemic context code provided on the support element. The glycemic context code can be machine-readable. The glycemic context code signals a glycemic context to a test strip meter, either upon insertion of the diagnostic test strip or by a user manually inputting the glycemic context into the test strip meter. A method for performing a guided structured test is also provided.

33 Claims, 10 Drawing Sheets

| 1 PP PB | 2 PP PB | 3 PP PB | 4 PP PB | 5 PP PB | 6 PP PB | 7 PP PB |
|---|---|---|---|---|---|---|
| 8 PP PB | 9 PP PB | 10 PP PB | 11 PP PB | 12 PP PB | 13 PP PB | 14 PP PB |
| 15 PP PB | 16 PP PB | 17 PP PB | 18 PP PB | 19 PP PB | 20 PP PB | 21 PP PB |
| 22 PP PB | 23 PP PB | 24 PP PB | 25 PP PB | 26 PP PB | 27 PP PB | 28 PP PB |
| 29 PP PB | 30 PP PB | 31 PP PB | | | | |
| | | | | | | |

GUIDED STRUCTURED TESTING KIT

TECHNICAL FIELD

This application generally relates to a guided structured testing kit, and more particularly relates to a guided structured testing kit comprising at least one diagnostic test strip that signals a glycemic context to a test strip meter.

BACKGROUND

In order to support glucose pattern testing, it is necessary to know the glycemic context of a blood glucose test. Devices that require a user to manually input or select the glycemic context of a particular blood glucose test often result in problems. Users may mistakenly select or input the wrong glycemic context associated with a particular test. Other users may fail to select or input a glycemic context altogether. Furthermore, many compact, easy-to-use test strip meters are not be compatible with a user interface that would support the input of a glycemic context associated with a blood glucose test. The glycemic context for one or more tests may be forgotten if a user has to wait to input the glycemic context until they reach a computer or other data-input device.

Accordingly, there remains a need for a glucose testing system that provides an improved way to associate the glycemic context with a blood glucose test result.

SUMMARY

In accordance with one embodiment of the present disclosure, a diagnostic test strip comprises a support element, a glucose reagent provided on the support element, and a glycemic context code provided on the support element. The glycemic context code may signal a glycemic context to a test strip meter upon insertion of the diagnostic test strip.

In accordance with another embodiment of the present disclosure, a guided structured testing kit is presented. The guided structured testing kit comprises a test strip container, a test strip meter, a testing protocol advisor, and at least one of a diagnostic test strip. The at least one of the diagnostic test strip comprises a support element, a reagent provided on the support element, and a glycemic context code provided on the support element. The glycemic context code signals a glycemic context to the test strip meter upon insertion of the at least one diagnostic test strip. The test strip container defines an internal volume to hold the at least one diagnostic test strip and the testing protocol advisor notifies a user of an at least one glycemic testing protocol.

In accordance with another embodiment of the present disclosure, a method for performing a guided structured test is presented. The method comprises providing a diagnostic test strip having a glycemic context code and a test strip meter. The method may also comprise signaling a glycemic context to a test strip meter from the glycemic context code and associating the signaled glycemic context with a blood glucose test result provided by the diagnostic test strip.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which:

FIG. 6 shows a glycemic testing protocol in accordance with yet another embodiment of the present invention.

DETAILED DESCRIPTION

Figure 1A:
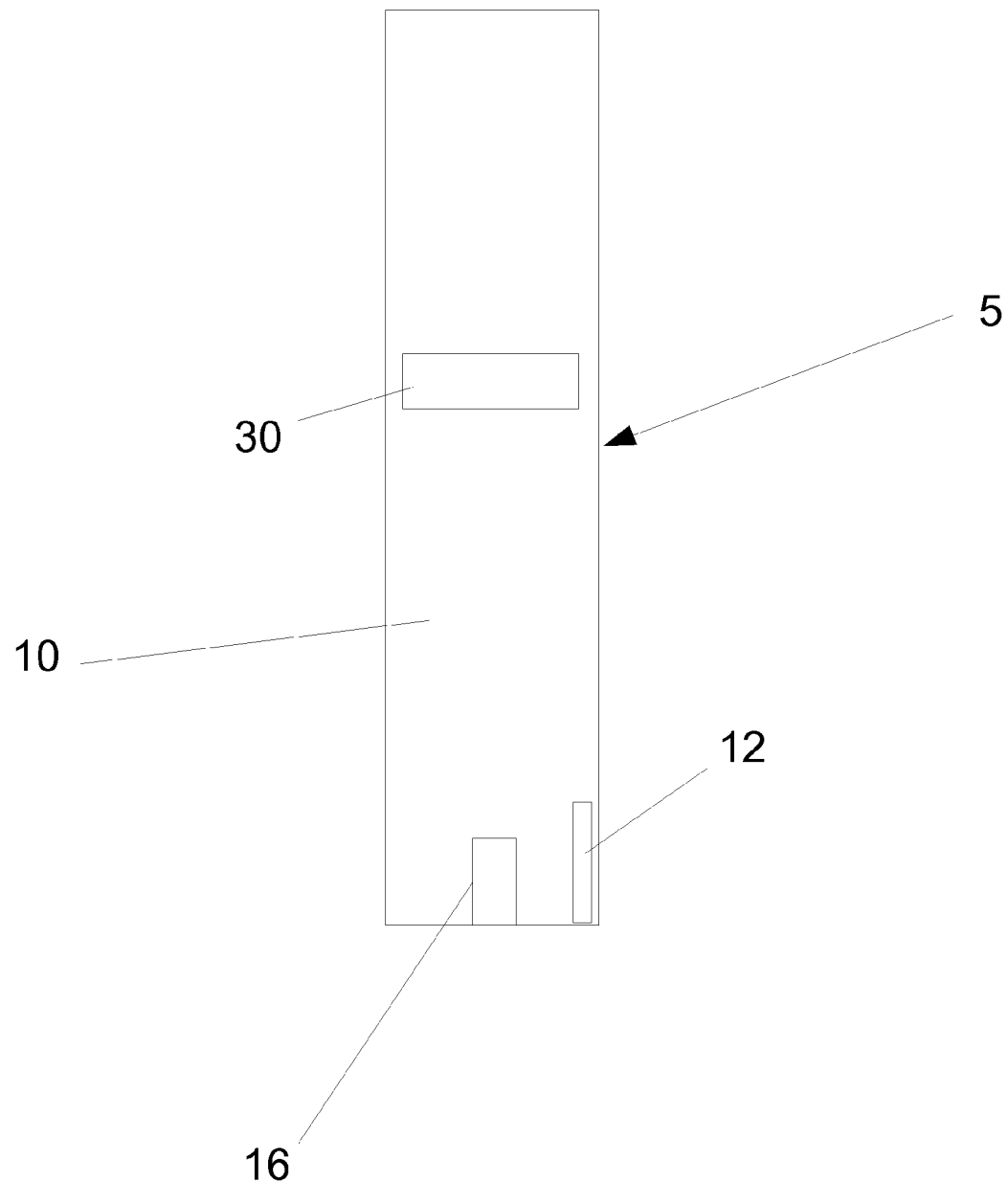
FIGS. 1A-D show front views of diagnostic test strips in accordance with one or more embodiments of the present invention.

Referring initially to FIG. 1A, in one embodiment, a diagnostic test strip 5 is provided. The diagnostic test strip may comprise a support element 10, a glucose reagent 16 provided on the support element, and a glycemic context code 12 provided on the support element. In one exemplary embodiment, the glycemic context code 12 can be machine-readable by, for example, a medical device meter such as a blood glucose meter or the like. The glycemic context code signals a glycemic context to a test strip meter 14 (as shown in FIG. 2) upon insertion of the diagnostic test strip.

In further describing the embodiments of the present disclosure, a conventional test strip may be referenced. Examples of such test strips suitable for use with the subject disclosure include those described in U.S. Pat. Nos. 6,193, 873; 6,475,372; 6,716,577; 6,620,310; and 6,558,528; the disclosures of which are herein incorporated by reference. The length of the test strip 5 generally ranges from about 3 mm to about 1000 mm, or from about 10 mm to about 100 mm, or from about 20 mm to about 60 mm. The support element may comprise a flexible plastic or similar material suitable to provide a machine-readable glycemic context code to a test strip meter. The reagent 16 may comprise a material or device suitable to indicate the levels of glucose provided in an assay of blood, as will be appreciated by one of ordinary skill.

Referring further to FIG. 1A, the diagnostic test strip 5 may also comprise a glycemic context code 12. In one example embodiment, the glycemic context code 12 can be machine-readable. The glycemic context code 12 may be provided on any portion of the support element 10. In one embodiment, the glycemic context code 12 is provided on one end of the test strip 5. However, it is also contemplated that the glycemic context code 12 may be provided at any location along the test strip 5, suitable to signal the glycemic context to a test strip meter. The glycemic context code 12 may be provided on the same end of the diagnostic test strip 5 as the reagent 16. The glycemic context code 12 may be oriented on the support element 10 such that it does not interfere with the blood glucose testing functionality of the reagent 16.

Figure 2:
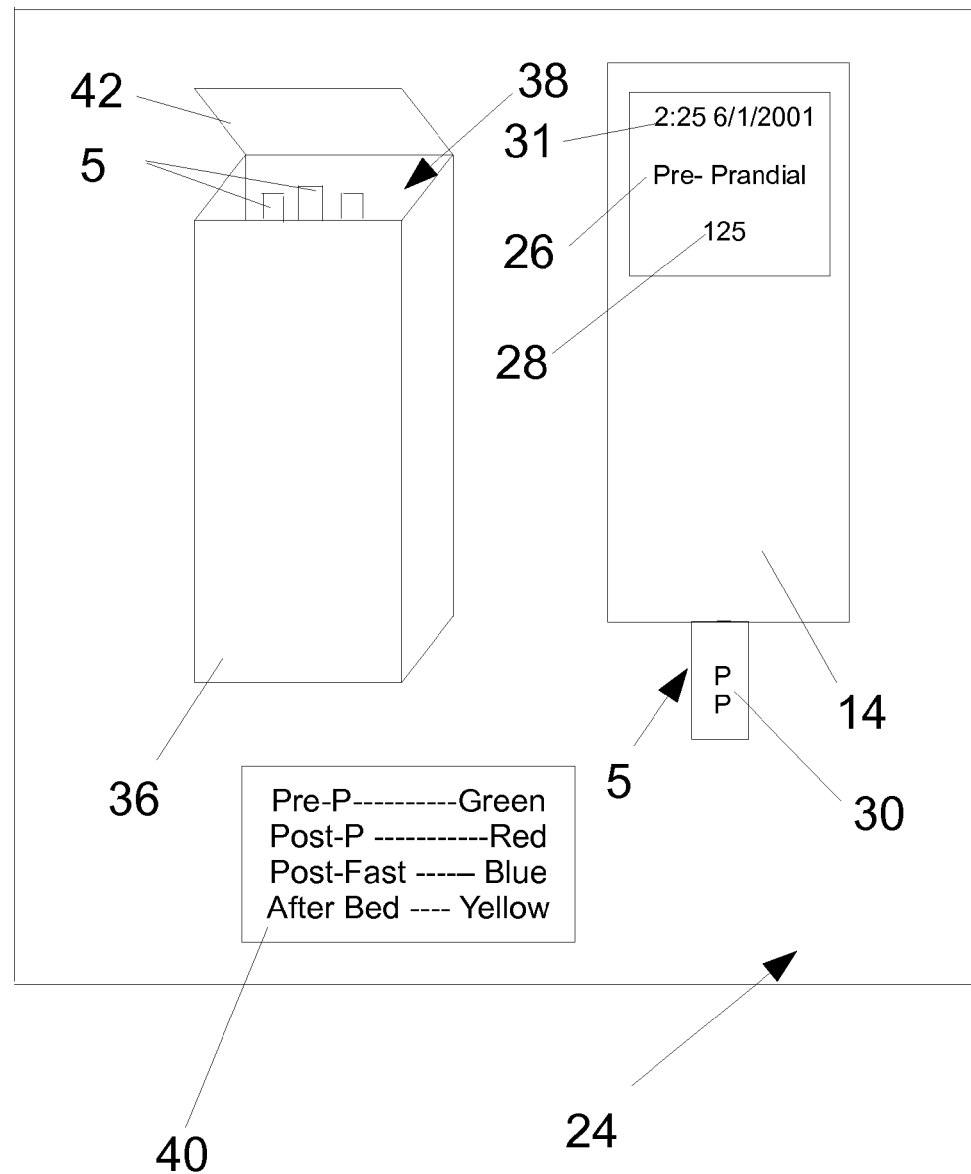
FIG. 2 shows a structured testing kit in accordance with another embodiment of the present invention.

In one embodiment, the glycemic context code 12 allows the glycemic context 26 of a performed blood glucose test to be signaled to a test strip meter 14 by simply inserting a diagnostic test strip 5 into the test strip meter 14 (as shown in FIG. 2). Once the glycemic context code 12 is inserted into the test strip meter 14, the test strip reader may read the glycemic context code 12, and receive the glycemic context 26 associated with the diagnostic test strip 5. In another embodiment, the test strip meter 14 could have an external reader that can, for example, optically scan the glycemic context from the diagnostic test strip 5 to receive the glycemic context 26 associated with the diagnostic test strip 5. In yet another embodiment, the glycemic context 26 of a performed blood glucose test associated with the diagnostic test strip 5 can be manually inputted into a test strip meter 14 by the user. In one embodiment, the user can simply type-in the glycemic context 26 using an input device, such a keyboard, touch screen or the like. In another embodiment, the user can select the glycemic context 26 by a user interface, such as, a graphical user interface, on the test strip meter 14. The graphic user interface may comprise a series of drop down text boxes, radio buttons or combinations of any suitable known user interface. In one embodiment, the graphical user interface can provide a choice of symbols related to the glycemic context 26 which can be associated with the glycemic context code 12 on the diagnostic test strip 5 or a test strip container. For storing the glycemic context 26 together with the blood glucose value, the user just has to choose the symbol for the glycemic context 26 displayed on the graphical user interface which is similar to the symbol for the glycemic context 26 on the diagnostic test strips 5 that was used for the blood glucose measurement. Once the glycemic context code 12 associated with the diagnostic test strip 5 is inputted into the test strip meter 14, the test strip meter 14 may then assign the glycemic context 26 to the blood glucose test result of that particular diagnostic test strip 5.

Each diagnostic test strip 5 may include a glycemic context code 12 designed to signal the intended glycemic context 26 to the test strip meter 14. By changing the glycemic context code 12, the glycemic context 26 signaled to the test strip meter 14 changes. Therefore, by modifying the glycemic context code 12 embedded on each test strip 5, a comprehensive glycemic testing procedure may be provided, such that a variety of test strips 5 may be provided in a kit suitable to signal all possible glycemic contexts 26 to the test strip meter 14.

Referring generally to FIGS. 1A-1D, the glycemic context code 12 may comprise a range of signaling indicia that may be read by, scanned into or inputted into the test strip meter 14 (as shown in FIG. 2) to communicate the intended glycemic context 26. The glycemic context 26 may be defined as any event that may have a significant impact on blood glucose levels of an individual. In other words, the glycemic context 26 defines the conditions under which a blood glucose measurement has to be executed by a user. In particular, rules define conditions which determine the time or time window for a blood glucose measurement and/or at least one action of a user which has to be executed directly in connection with a blood glucose measurement and/or actions which are chronologically related to the measurements so that the action may impact the blood glucose measurement. For example, the time, or the time windows, for taking the blood glucose measurement and/or further actions can be determined by the conditions that have to be executed before or after that measurement, e.g., fasting or pre and post-prandial. The glycemic context code 12 may be selected from the group including, but not limited to, an optical signaling indicia 18, an electrical signaling indicia 20, a mechanical signaling indicia 22, and combinations thereof. Alternatively, other signaling indicia may be used suitable to convey a glycemic context 26 to a test strip meter 14 by, for example, upon insertion of a diagnostic test strip 5, manual input into the test strip meter 14, or scanning a diagnostic test strip 5.

Figure 1B:
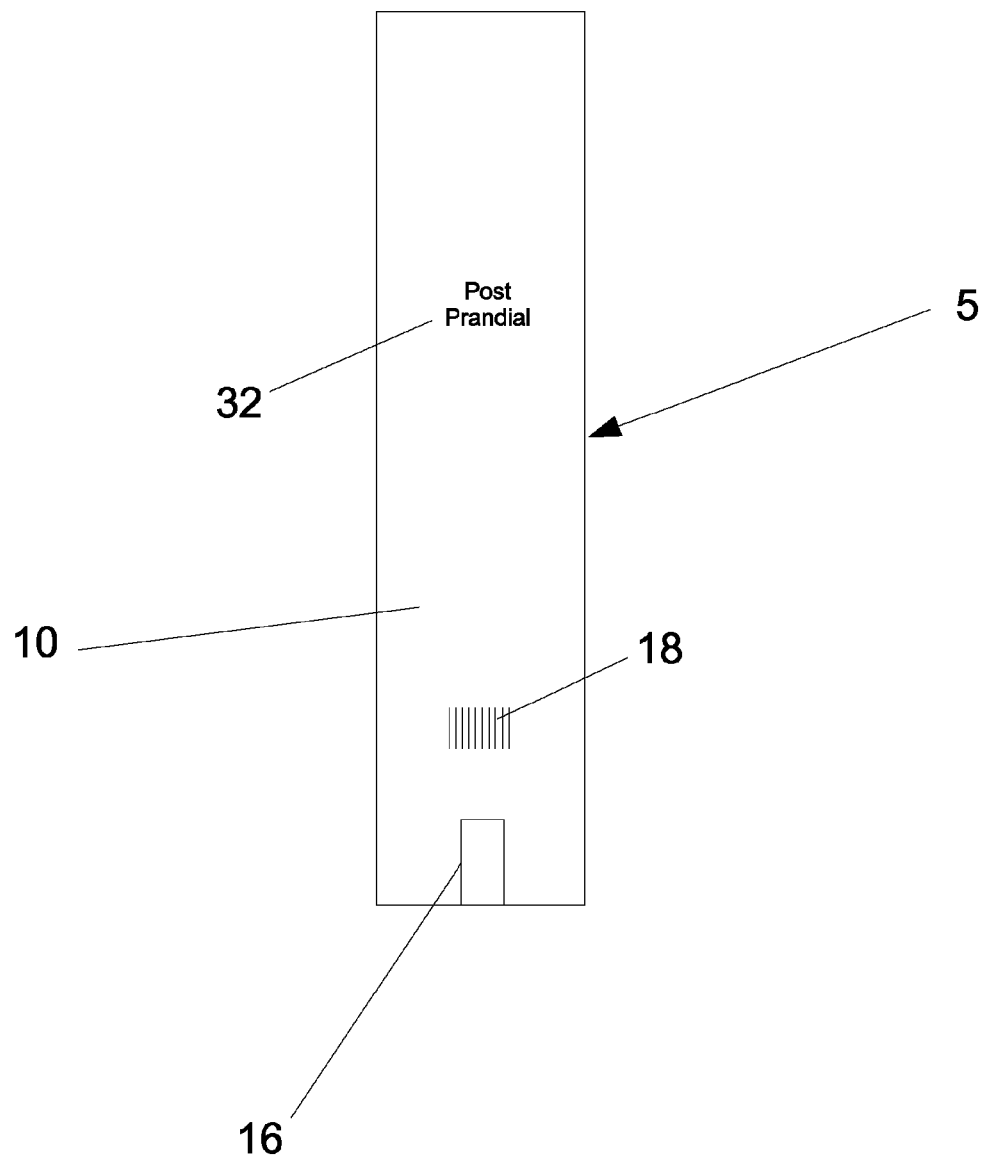

Referring to FIG. 1B, in one embodiment, the glycemic context code 12 may comprise an optical signaling indicia 18. The optical signaling indicia 18 may be selected from the group, but not limited to, a bar code, a hole pattern, and combinations thereof. The test strip meter 14 may sense the optical signaling indicia 18, and recognize the particular glycemic context associated therewith, as will be appreciated by one of ordinary skill.

Figure 1C:
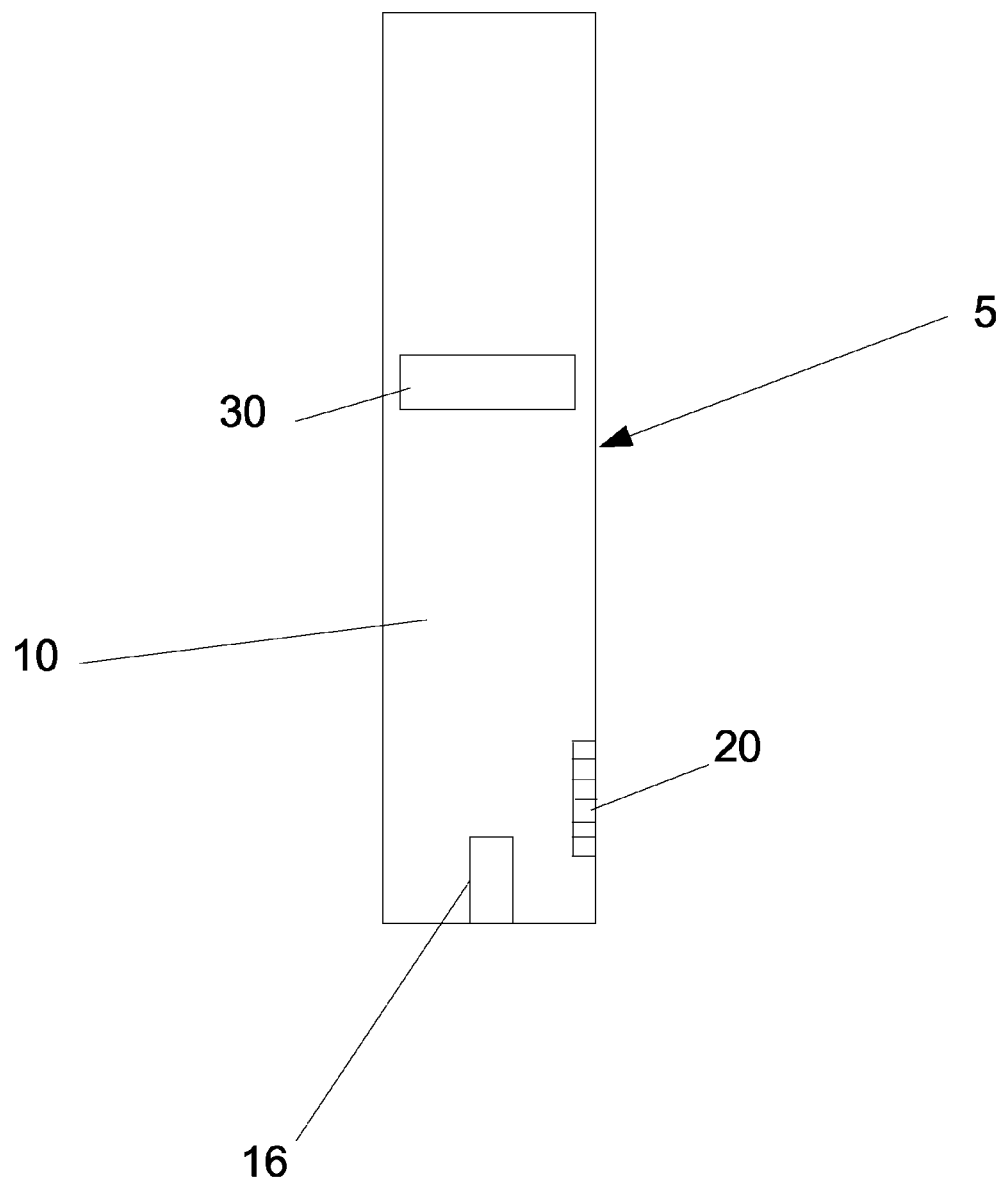

Referring to FIG. 1C, in one embodiment, the glycemic context code 12 may comprise an electrical signaling indicia 20. The electrical signaling indicia 20 may be selected from the group, but not limited to, a distinctive resistance, capacitance, break pattern, and combinations thereof. Other types of electrical signaling indicia 20 are also contemplated, as will be appreciated by one of ordinary skill.

Figure 1D:
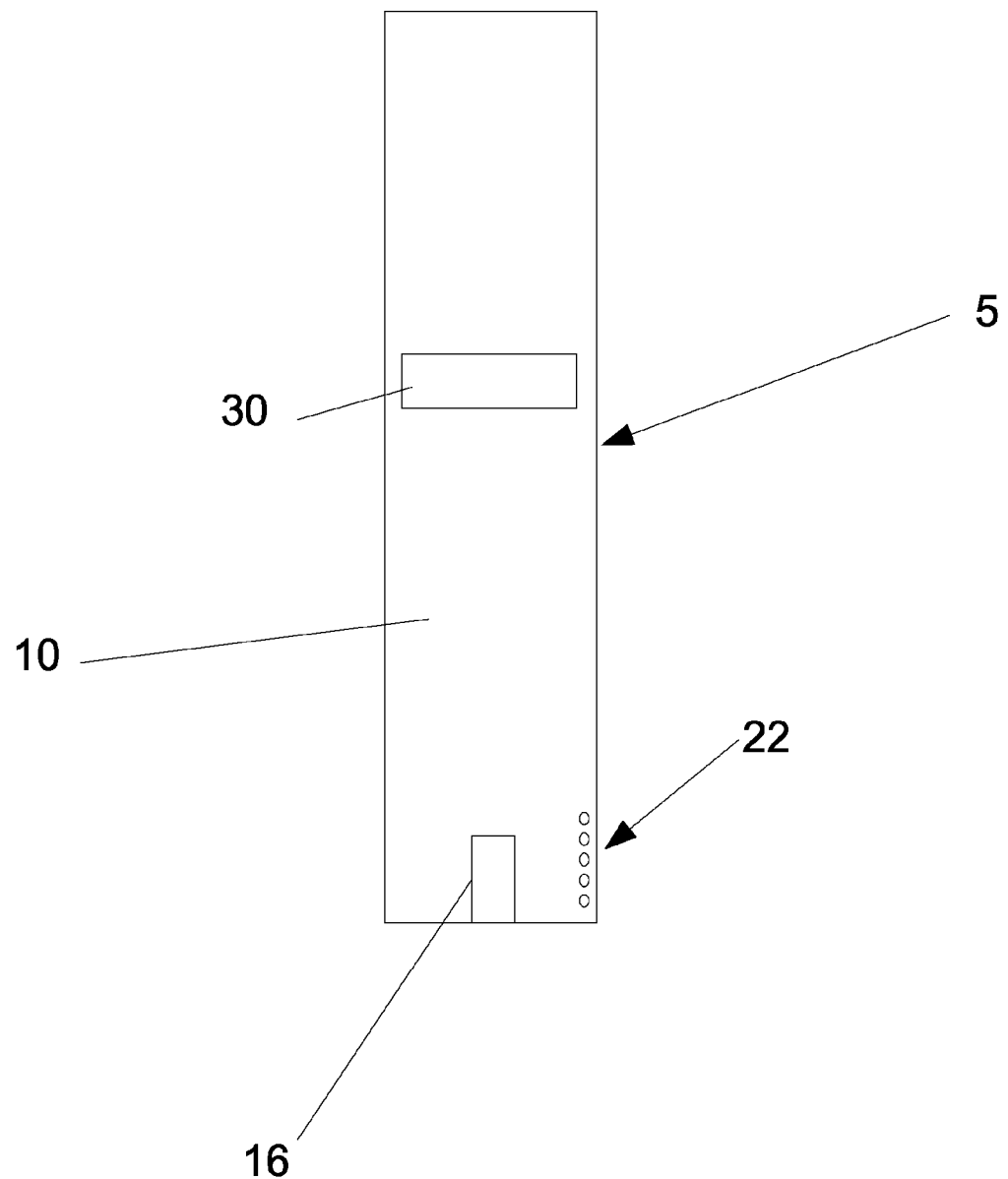

Referring to FIG. 1D, in one embodiment, the glycemic context code 12 may comprise a mechanical signaling indicia 22. The mechanical signaling indicia 22 may be selected from the group, but not limited to, an indent pattern, a hole pattern, strip width or combinations thereof. It is also contemplated that other forms of mechanical, optical, and electrical signaling indicia may be used in conjunction with the methods and devices disclosed herein, as will be appreciated by one of ordinary skill, such as RFID, wireless adapters, dyes, magnetic encoding, and similar communication interfaces.

Referring to FIG. 2, in one embodiment, a guided structured testing kit 24 is provided. The guided structured testing kit 24 may comprise a test strip meter 14. The test strip meter 14 may be configured and designed to interact with the type of signaling indicia provided on the diagnostic test strips 5 as described above. The test strip meter 14 may be suitable to detect the blood glucose levels present in the blood sample provided on the inserted diagnostic test strip 5. The test strip meter 14 may comprise a code reader (not shown), configured and designed to read the signals provided by the glycemic context codes 12. In one embodiment, the code reader can be internal to the test strip meter 14. In another embodiment, the code reader can be external to the test strip meter 14. Alternatively, the test strip meter 14 may have the glycemic context codes 12 manually inputted into the test strip meter 14.

The code reader may be an optical code reader, a mechanical code reader, or an electrical code reader. More generally, the code reader may be selected to correspond to the type of signaling indicia provided on the diagnostic test strips 5 that will be used in conjunction with the test strip meter 14. Accordingly, in one embodiment, if there is an internal code reader, when a test strip 5 is inserted into the test strip meter 14 having a glycemic context code 12, the test strip meter 14 may read the glycemic context 26 associated with the particular glycemic context code 12, and associate that glycemic context 26 with the blood glucose test result. In another embodiment, if there is external code reader, the test strip meter 14 may optically scan the glycemic context code 12 and read the glycemic context 26 associated with that particular glycemic context code 12 on the diagnostic test strip 5 and associate that glycemic context 26 with the blood glucose test result. Alternatively, a user can input the glycemic context 26 associated with the particular glycemic context code 12 on the test strip 5 into the test strip meter 14, and the test strip meter 14 can then associate that glycemic context 26 with the blood glucose test result.

The test strip meter 14 may be designed to store the glycemic context 26 communicated by the diagnostic test strip 5 in a local memory system. The test strip meter 14 may associate the glycemic context 26 with the blood glucose test result 28, and assign a date and time stamp 31 for the test for subsequent download to a program to aid in the analysis of blood glucose trends and patterns. The memory system (not shown) may be configured to store and analyze a plurality of blood glucose test results, and their corresponding glycemic contexts 26 for later upload and assessment.

The glycemic context 26 represents the intended usage of the diagnostic test strip 5 in terms of the glycemic events that a user of a diagnostic test strip 5 would experience. As was described previously, the glycemic context 26 may be defined as any event or condition that may have a significant impact on blood glucose levels of an individual. The glycemic context 26 may be selected from the group including, but not limited to, taking a pre-prandial measurement and/or post-prandial measurement, taking a pre- and/or post-event measurement, executing an event like exercise, taking the action to remain fasting or taking medication, taking a bedtime measurement, taking the action to sleep, for example, for at least a predetermined period of time, and combinations thereof. Other glycemic events may include pre-, or post-exercise, pre- or post-nap, pre- or post-snack, and other similar glycemic events as will be appreciated by one of ordinary skill. By supplying the glycemic context 26 in conjunction with the blood glucose test result, more information may be obtained for a particular test subject.

It is contemplated that a plurality of diagnostic test strips 5 may be provided to a user. The diagnostic test strips 5 may be provided to a user in groups, pertaining to their encoded glycemic contexts 26. Each group of diagnostic test strips 5 may be configured to signal a different glycemic context 26. For example, the groups may include approximately ten diagnostic test strips 5 having glycemic context codes 12 configured to signal a pre-prandial glycemic context 26; approximately ten diagnostic test strips 5 configured to signal a post-prandial glycemic context 26; and approximately ten diagnostic test strips 5 configured to signal a fasting glycemic contexts 26. Other group sizes and groupings may also be provided, as will be appreciated by one of ordinary skill. Therefore, a user may select from the plurality of test strips 5, a diagnostic test strip 5 having a glycemic context code 12 appropriate to signal the proper glycemic context 26 pertaining to the user's glycemic state.

Referring again to FIG. 1A, in another embodiment, the glycemic context code 12 may be readily identified by the user by, for example, look or feel such that the glycemic context code 12 can suitably convey the glycemic context 26 associated with a particular diagnostic test strip 5 to the user. For example, a diagnostic test strip 5 having a glycemic context code 12 configured to signal a pre-prandial glycemic context 26 may have a blue color strip. In another example, a diagnostic test strip 5 having a glycemic context code 12 configured to signal a pre-prandial glycemic context 26 may have a round hole. Each glycemic context 26 may have a distinct glycemic context code 12, so a user can quickly identify which diagnostic test strip 5 is configured to signal the appropriate glycemic context 26.

Referring to FIG. 2, in one configuration, the glycemic context code 12 may be readable by the test strip meter 14 and may communicate to a test strip user the intended glycemic context 26 of the test strip 5. Accordingly, in one embodiment, the glycemic context code 12 is both machine-readable and identifiable by a user. For example, the glycemic context code 12 may comprise a particular color. The test strip meter 14 may comprise a code reader configured to associate a particular color with a particular glycemic context 26. Similarly, a user of the test strip 5 may be instructed to associate a particular test strip color with the intended glycemic context 26. It is also contemplated that the glycemic context code 12 may signal to a test strip meter 14, the glycemic context 26, through color coding, textual signals, patterns, and other forms as will be appreciated by one of ordinary skill.

The glycemic context code 12 may be selected from the group, including, but not limited to, a color code; a tactile code, a label 32 (FIG. 3); and/or combinations thereof. For example, the glycemic context code 12 may comprise a band of color or the entire test strip 5 may be colored to correspond to the particular glycemic context 26.

In one configuration, the glycemic context code 12 may comprise a color-coded strip identifier, where each color is associated with a particular glycemic context 26. The color code may be located along the support element 10 in a range of configurations, such as a strip of colored material, or the entire strip may be colored, to correspond to a particular glycemic context 26. For example, a black strip identifier may indicate the glycemic context 26 of fasting. Therefore, a user should select a black strip identifier after they have been fasting for a certain period of time and wish to perform a blood glucose test. Similarly, a red glycemic context code 12 may be associated with diagnostic test strips 5 intended for a post-prandial glycemic context 26. In this case, the user should select a red glycemic context code 12 after a predetermined period of time after a meal to perform a blood glucose test.

Figure 3:
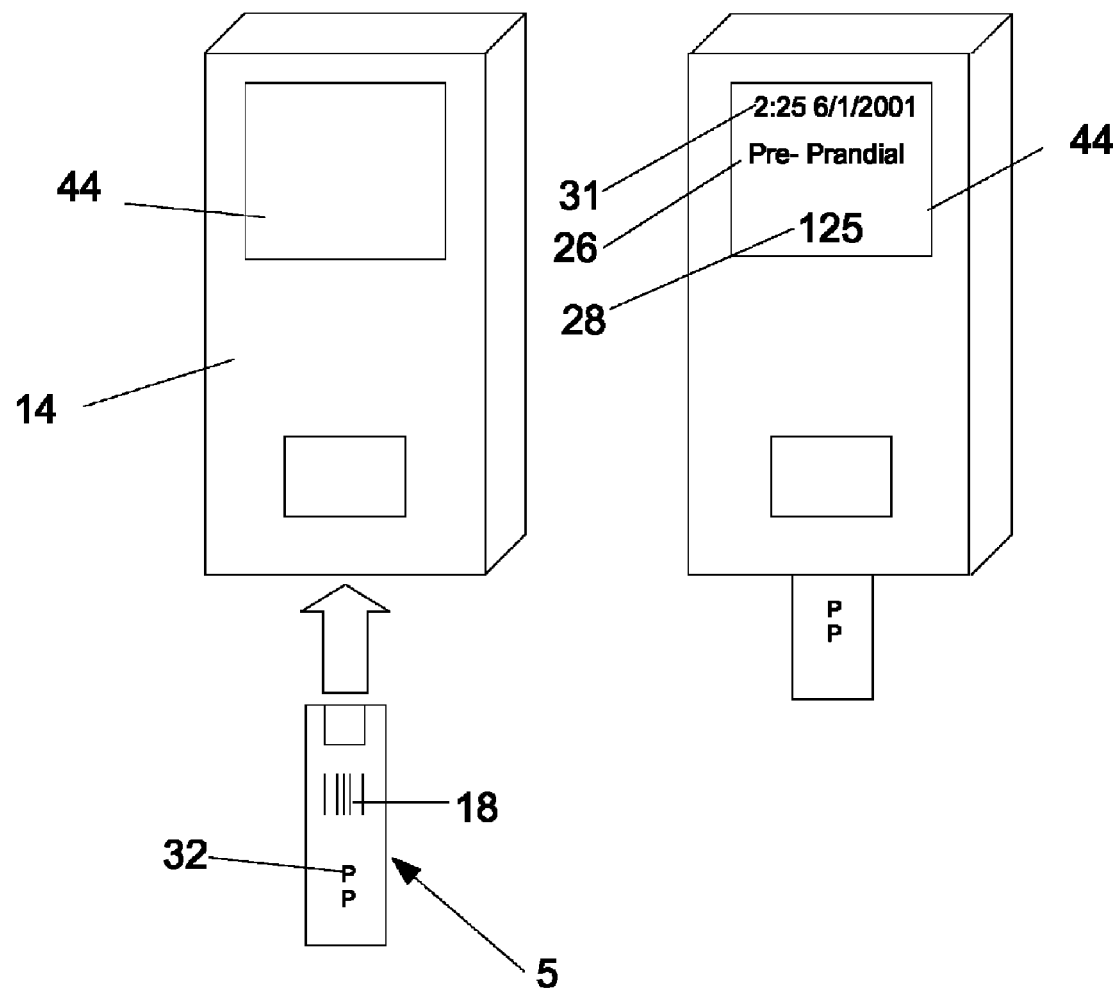
FIG. 3 shows a schematic view of a test strip meter in combination with a diagnostic test strip of FIGS. 1A-D in accordance with yet another embodiment of the present invention.
Figure 4:
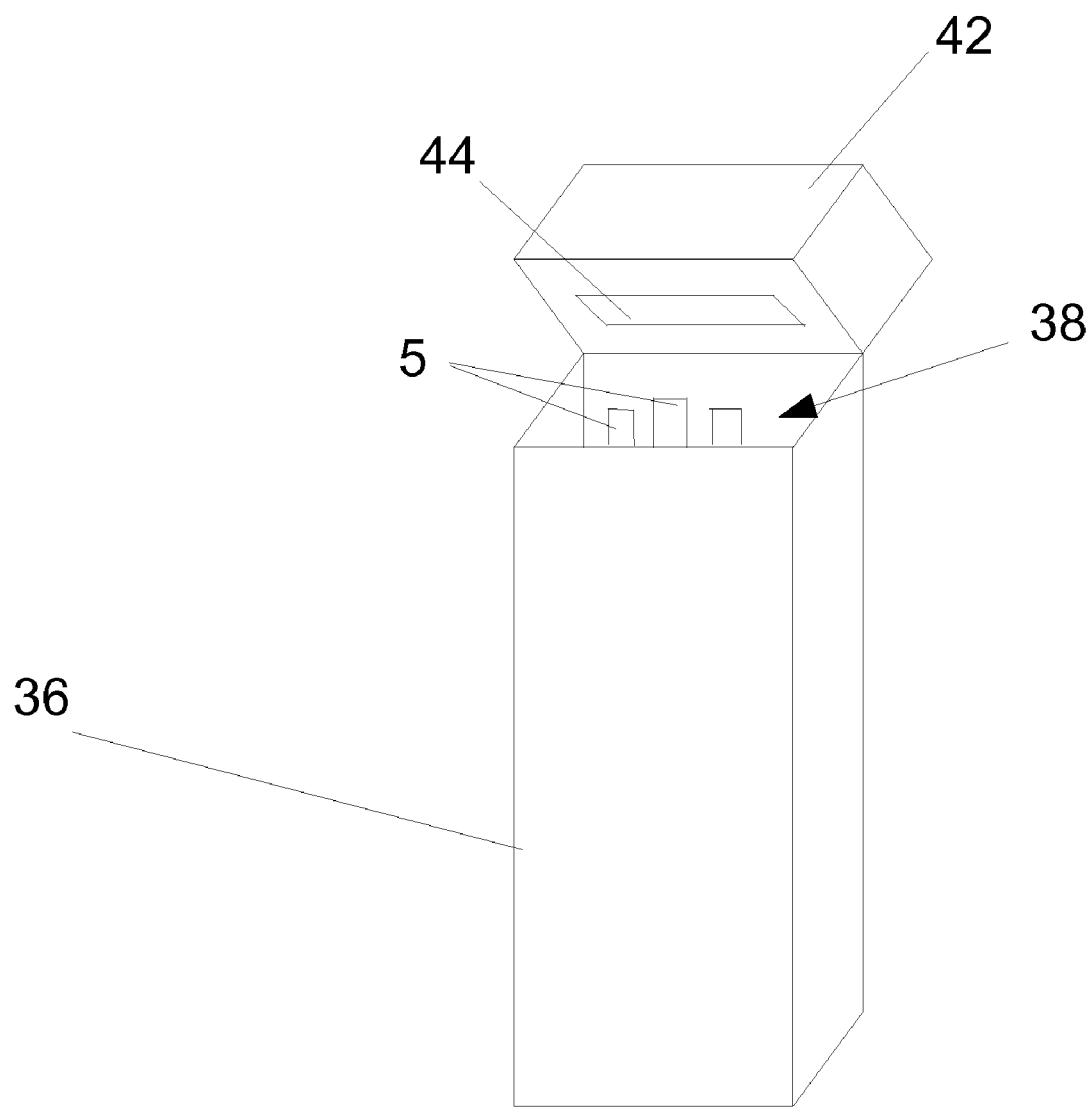
FIG. 4 shows a front perspective view of test strip container in accordance with one embodiment of the present invention.

Referring to FIG. 3, in one embodiment, the glycemic context identifier 30 may comprise a label 32. The label 32 may indicate textually or symbolically the intended glycemic context 26 of a particular test strip 5. The glycemic context identifier 30 may also comprise a particular strip shape, texture, or other distinctive marking suitable to indicate to a user the intended glycemic context 26 of the diagnostic test strip 5. The glycemic context identifier 30 may also comprise a distinctive wrapper (not shown) for each targeted glycemic context 26. For example, each wrapper color may be associated with a particular glycemic context 26. The wrapper may comprise a distinctive label 32 which indicates its targeted glycemic context 26 in addition to a particular color.

Referring again to FIG. 2, the guided structured testing kit 24 may comprise a test strip container 36, a test strip meter 14, a testing protocol advisor (not shown), and at least one of the diagnostic test strips 5 described above. In one embodiment, the test strip container 36 may define an internal volume 38 configured to contain at least one of the diagnostic test strips 5. The test strip container 36 may comprise a range of shapes and configurations, such as rectangular, elliptical, rounded, and other shapes. The test strip container 36 may be sealed to prevent the ingress of moisture through cooperation with a lid. In addition, in one example embodiment, the test strip container 36 may be integrated in combination with the test strip meter 14 as a single device.

Figure 5:
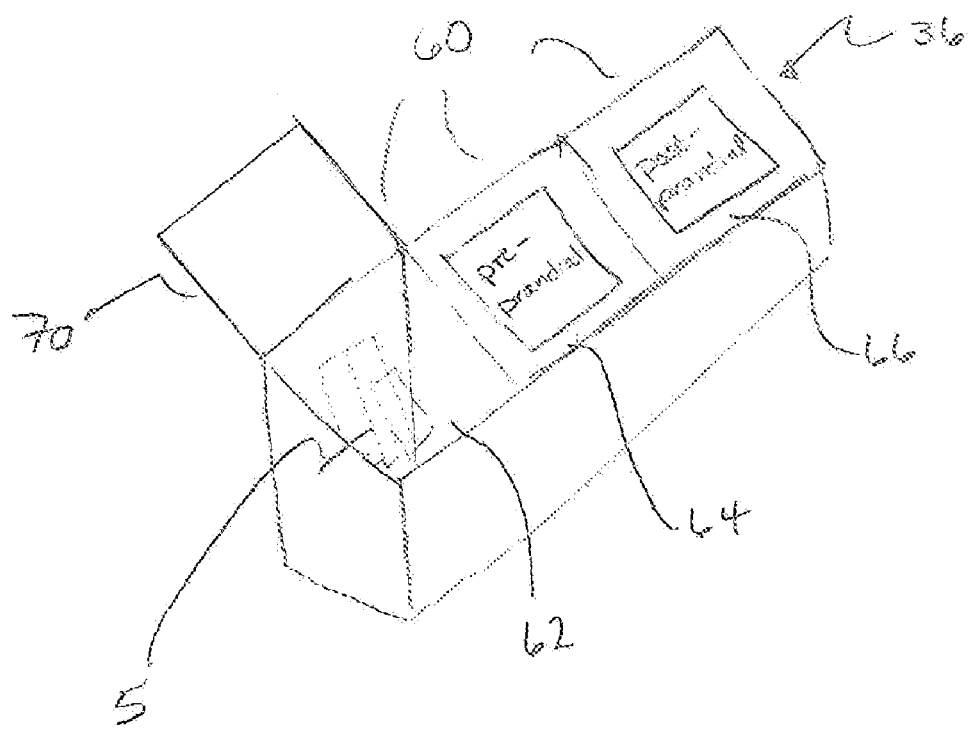
FIG. 5 shows an alternative test strip container in accordance with one embodiment of the present invention.

In another embodiment, the test strip container 36 can have a plurality of compartments 60, and within each of the plurality of compartment, a plurality of diagnostic test strips 5 having related glycemic context code 12 can be housed. For example, as illustrated in FIG. 5, a three-compartment test strip container 36 could be configured so that in the first compartment 62, the fasting diagnostic test strips 5 are housed; in the second compartment 64, the pre-prandial diagnostic test strips 5 are housed; and in the third compartment 66, the post-prandial diagnostic test strips 5 are housed. In addition, the plurality of compartments 60 can be have lids 70 to prevent the ingress of moisture and can be labeled such that the user can easily identify the glycemic context code 12 for each diagnostic test strip 5 by, for example, labeling the top of the compartments 60 with the type of diagnostic test strip 5 contained within. In contrast to having the glycemic context code 12 directly on the diagnostic test strip 5, the glycemic context code 12 can be also somewhere on/or in the test strip container 36 so that the glycemic context code 12 for the related test strip 5 is assigned to the associated compartment 60 of the test strip container 36. For example, different glycemic context codes 12 can be labeled on the lids 70 of the compartments 60 so that different compartments 60 can be assigned to different glycemic context codes 12. By labeling the compartments 60, the glycemic context code 12 can be related to the diagnostic test strips 5 within the compartment 60 of the test strip container 36 so that a diagnostic test strip 5 can be assigned a glycemic context code 12 even if the glycemic context code 12 is not directly on the diagnostic test strip 5 itself.

Although a three compartment test strip container 36 is described, it can be envisioned that other pluralities of compartments 60 could be used without deviating from the scope of the present disclosure such as, for example, a seven compartment test strip container 36, wherein each compartment 60 represents a day of the week and houses the diagnostic test strips 5 that need to be used for that particular day; a two compartment test strip container 36, wherein one compartment 60 contains a pre-event diagnostic test strips 5 and the other compartment 60 contains post-event diagnostic test strips 5, such as, for example, pre- and post-exercise; or any other suitable plurality of compartment test strip containers 36.

The guided structured testing kit 24 may comprise a context code identifier legend 40. The context code identifier legend 40 may comprise instructions that indicate which glycemic context code 12 is associated with each glycemic context 26 to prevent the use of an improper test strip(s) 5 with a different glycemic context 26. The context code identifier legend 40 may be provided as a separate document or instruction manual in some embodiments, or in other embodiments, may be integrated into the guided structured testing kit 24, the test strip container 36 or the test strip meter 14, or may be digitally displayed.

Figure 7:
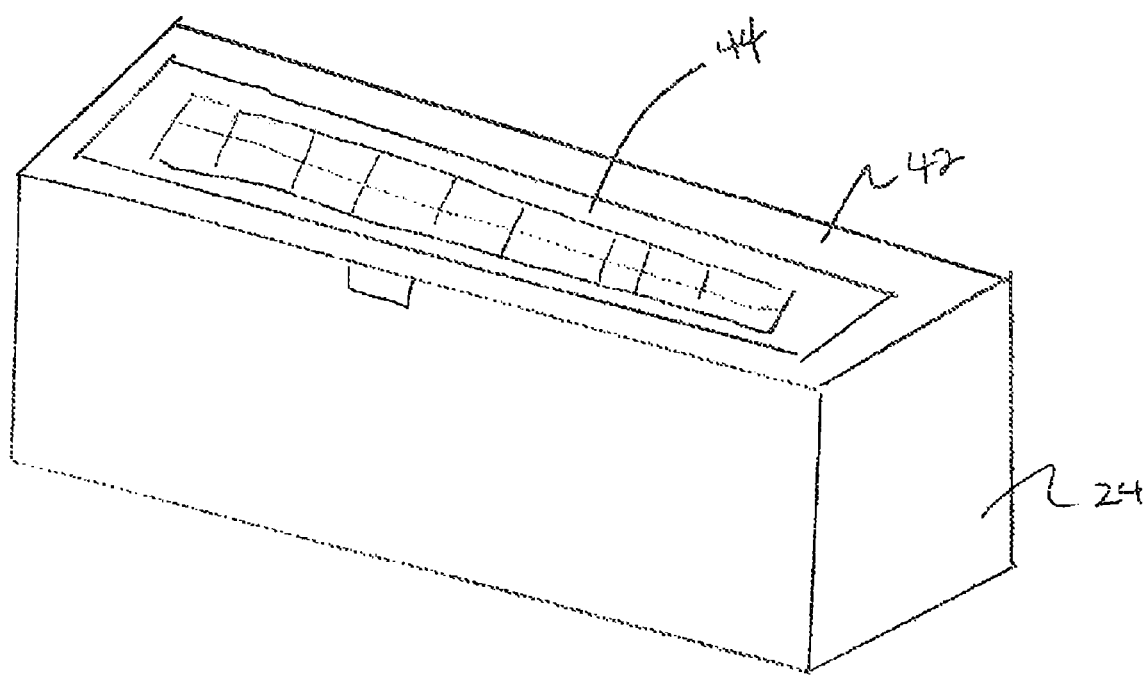
FIG. 7 shows an exterior view of a structured pattern testing kit in accordance with one embodiment of the present invention.

Referring to FIG. 7, in another embodiment, the guided structured testing kit 24 can comprise a lid 42. The lid 42 may comprise a display 44. The display 44 may be configured to provide a visual notification to a user of at least one glycemic testing protocol 46. Alternatively, the display 44 may be provided on the test strip meter 14 (FIG. 3).

The visual notification may comprise a calendar comprising appointments organized by dates. The visual notification may also be a signal indicative of the time of the testing, and type of context. The display 44 may comprise an e-paper display, LED, OLED, or other display system as will be appreciated by one of ordinary skill. The visual notification may comprise an icon, or textual message to the user to perform a blood glucose test, and may indicate which glycemic context code 12 or what glycemic context 26 is being targeted.

Referring to FIG. 6, a testing protocol advisor may notify a user of at least one glycemic testing protocol 46. In one example embodiment, the testing protocol advisor may be implemented as a paper tool. The paper tool may be provided to the user, for example, as a hardcopy or it may be downloaded and printed. In one embodiment, the paper tool testing protocol advisor can be attached to the guided structured testing kit 24 by, for example, adhesive or the like. The paper tool testing protocol advisor can be attached to the guided structured testing kit 24 in such a way that the paper tool can be easily visible to the user. In one example embodiment, as illustrated in FIG. 7, the paper tool testing protocol advisor can be displayed on the outside top of the lid 42 of the guided structured testing kit 24. In another embodiment, the paper tool testing protocol advisor can be displayed on the inside of the lid 42 of the guided structured testing kit 24. In yet another embodiment, the paper tool testing protocol advisor can be displayed on a side of the guided structured testing kit 24 or any other foreseeable location.

In another example embodiment, the testing protocol advisor may comprise a programmed functionality embodied on a processor and memory system (not shown). The testing protocol advisor may be integrated into the guided structured testing kit 24, or the test strip meter 14. The testing protocol advisor may comprise a processor and memory device, programmed to perform the functions described throughout the application. The testing protocol advisor may be integrated into the memory system and processor of the test strip meter 14 in some embodiments, or in other embodiments, may be comprised as a stand-alone processor and memory system.

The glycemic testing protocol 46 may comprise a plurality of scheduled tests 48. Each scheduled test 48 may comprise a date/time stamp, and a glycemic context 26. The plurality of scheduled tests 48 may be pre-arranged according to the patient's recommended testing routine, with a certain number of blood glucose tests performed each day, at certain times and glycemic contexts 26.

In one configuration, the test protocol advisor may associate at least one of the scheduled tests 48 with a glycemic context 26 as described above. Accordingly, when a blood glucose test is conducted near the date/time and glycemic context 26 of a scheduled test 48, the testing protocol advisor may automatically associate a test result with the scheduled test 48. Alternatively, a user may manually associate a blood glucose test result 28 with at least one scheduled test 48, and at least one glycemic context 26. Additional testing protocols 46 may be programmed and selected, as may be desired by a user.

Referring again to FIG. 2, in another embodiment, if a diagnostic test strip 5 is inserted into, or scanned by, the test strip meter 14, or alternatively, if the user manually enters a glycemic context 26 of the diagnostic test strip 5 into the test strip meter 14, that indicates a glycemic context 26 incompatible with the glycemic context 26 associated with the scheduled test 48, the test strip meter 14 may be configured to present a signal to the user that the diagnostic test strip 5 has a glycemic context code 12 programmed for a different glycemic context 26 than prescribed. The test protocol advisor may be configured to notify the user what glycemic context 26 is targeted, and the glycemic context code 12 of the mistakenly inserted test strip 5. The signal may comprise a visual, audible, or mechanical signal, such as a vibration, flashing light, or beep. Referring to FIG. 6, in another configuration, if at least one scheduled test 48 is missed, the test strip meter 14 may signal to a user that a test should be performed.

In one embodiment, the glycemic testing protocol 46 may be programmable by a user to suit their own needs or schedule. The test protocol advisor may interact with a computer or similar textual input device to view and/or modify the testing protocol 46 and at least one scheduled test 48. The testing protocol 46 may be viewed using a calendar, with at least one scheduled test 48. The testing protocol 46 may be printed in a hard-copy format, or may be downloaded into guided structured testing kit 24 mentioned above. A variety of connection types are contemplated, as will be appreciated by one of ordinary skill.

Referring again to FIG. 2, in another embodiment, the test strip meter 14 can override the information of the glycemic context 26 indicated by the glycemic context code 12 of the diagnostic test strip 5. For example, if a user selects a "pre-fasting strip," and inserts it into the test strip meter 14, the test strip meter 14 may display a message to the user asking "Is this a pre-fasting test?" At this point, the test strip meter 14 may query the user to confirm the test, or pick an alternative glycemic context 26 from a presented list.

In another embodiment, the protocol advisor on the test strip meter 14 can query the user if the blood glucose measure value is not reasonable and/or plausible for the glycemic content code 12 of the used diagnostic test strip 5. For example, if a "pre-fasting" strip is selected and the test strip meter 14 measures an unreasonable high blood glucose value, the test strip meter 14 may display a message to user asking "Are you sure you fasted?" At this point, the test strip meter 14 may query the user to repeat the test, confirm the test, or pick an alternative glycemic context 26 from a presented list or any other foreseeable alternative. In another example, the test strip meter 14 can calculate the time stamps between an indicated pre-prandial test and an indicated post-prandial test. If the time difference between the two tests is outside an allowable predefined time window, the test strip meter 14 may display a message to user asking "Are you sure this is a post-prandial measurement?" The test strip meter 14 then may ask the user, in this example, to select another diagnostic test strip 5 and/or answer additional questions regarding potentially missing tests.

In yet another embodiment, the testing protocol advisor may comprise at least one strip sensor configured to detect when at least one of the scheduled tests 48 has been performed. The testing protocol advisor may review the results of the at least one scheduled tests 48 in the at least one glycemic testing protocols 46 and determine which scheduled tests 48 have been performed. The testing protocol advisor may assign a 'status' to each of the scheduled tests 48, corresponding to whether the test strip meter 14 has recorded a blood glucose test result for that scheduled tests 48.

The status of the at least one scheduled test strip 5 may comprise "completed," "missed," "late," and other indicators as will be appreciated by one of ordinary skill. The testing protocol advisor may be programmed to inform a user of a recommended action based on the status of the at least one scheduled glycemic test 48. For example, if the status of the at least one schedule glycemic test 48 is "missed," the testing protocol advisor may be programmed to inform a user that another blood glucose test should be performed for the next glycemic context 26. Alternatively, if the status is "missed," the testing protocol advisor may be programmed to inform a user to perform a blood glucose test immediately. It is also contemplated that the test protocol advisor may advise a user to perform other actions compatible with the glycemic testing protocol, such as exercise, eat, take insulin, or perform the next scheduled test.

In an exemplary embodiment, the glycemic testing protocol 46 may be a structured testing protocol such as those structured testing protocols described in U.S. patent application Ser. No. 11/424,757 filed Jun. 16, 2006 entitled "System and method for collecting patient information from which diabetes therapy may be determined;" U.S. patent application Ser. No. 12/643,338 filed Dec. 21, 2009 entitled "Structured Testing Method for Diagnostic or Therapy Support of a Patient with a Chronic Disease and Devices thereof;" and U.S. patent application Ser. No. 12/643,415 filed Dec. 21, 2009 entitled "Management Method and System for Implementation, Execution, Data Collection, and Data Analysis of a Structured Collection procedure which runs on a Collection Device," all of which are assigned to Roche Diagnostics Operations, Inc. and all of which are hereby incorporated by reference. The structured testing parameters may be preprogrammed into testing protocol advisor or may be manually programmed by the user or the user's health care provider. The structured testing parameters may be provided by (e.g., reside in memory of) the test strip meter 14, may be implemented as a paper tool, or may be a combination of both.

In one example embodiment of a programmed testing protocol advisor, it is to be appreciated that the processor of the testing protocol advisor can implement one or more structured glycemic testing protocol 46 provided in the memory device. Each structured glycemic testing protocol 46, in one example embodiment, can be stand-alone software, thereby providing the necessary program instructions which when executed by the processor causes the processor to perform the structured glycemic testing protocol 46 as well as other prescribed functions. In other embodiments, each structured glycemic testing protocol 46 can be part of the software, and can be then be selectively executed by the processor either via receiving a selection from a menu list provided in the display 44 in the lid 42. In another embodiment, the glycemic testing protocol 46 can be implemented as a paper tool. It is to be appreciated that the software, likewise, provides the necessary program instructions which when executed by the processor causes the processor to perform the structured glycemic testing protocol 46 as well as other prescribed functions of the software. One suitable example of having a selectable structured collection procedure provided as a selectable mode of a collection meter is disclosed by in U.S. patent application Ser. No. 12/491,523, filed Jun. 25, 2009, titled "Episodic Blood Glucose Monitoring System With An Interactive Graphical Diabetic person Interface And Methods Thereof," assigned to Roche Diagnostics Operations, Inc., which is hereby incorporated by reference now abandoned.

In still another embodiment, a command instruction can be sent from a health care provider's computer and received by the processor via a communication module (not shown), which runs automatically the structured glycemic testing protocol 46. Such a command instruction may specify which of the one or more structured collection procedures to run and/or provide a structured collection procedure to run. In still another embodiment, a list of defined medical use cases or medical questions can be presented on the display 44 by the processor, and a particular structured glycemic testing protocol 46 can be automatically chosen by the processor from a plurality of structured collection procedures depending on the selection of the defined medical use cases or medical questions received by the processor or can be manually selected by the user or the user's health care provider.

In still yet another embodiment, after selection, the structured glycemic testing protocol 46 can be provided through computer readable medium and loaded by the guided structured testing kit 24, or the test strip meter 14, downloaded from a computer, or a server. The server, for example, may be a healthcare provider or company providing such pre-defined structured glycemic testing protocol 46 for downloading according to a selected defined medical use case or question. It is to be appreciated that the structured glycemic testing protocol 46 may be developed by a healthcare company and implemented via a public network through a webpage and/or made available for downloading on the server. In still other embodiments, the processor may notice that a new structured glycemic testing protocol 46 is available for use on the guided structured testing kit 24 or the test strip meter 14 to help address a particular use case/medical question that a diabetic person (e.g., healthcare provider and patient) which can then be provided in any standard fashion, such for via postal letters/cards, email, text messaging, tweets, and the likes.

In some embodiments, as mentioned above previously, a paper tool can perform some of the functions provided by the diabetes software. An example of some of the functions which may be incorporated into the diabetes software and which is configured as a paper tool is the Accu-Chek® 360 View Blood Glucose Analysis System paper form available from Roche Diagnostics also disclosed in U.S. patent application Ser. No. 12/040,458 filed Feb. 29, 2007 entitled "Device and method for assessing blood glucose control," assigned to Roche Diagnostic Operations, Inc., which is hereby incorporated by reference.

In this structured testing embodiment, the glycemic testing protocol 46 may have structured testing parameters defining entry, exit and adherence criteria as defined in a structured testing protocol. The entry criteria can include criteria used to determine whether to begin data collection for the structured testing protocol. The entry criterion for this exemplary embodiment may be, for example, that the user has indicated a willingness to perform the structured testing protocol or that the user has maintained his/her blood glucose level for a predetermined period of time. However, any other suitable entry criterion is foreseeable.

The adherence criteria can include criteria used in accepting or rejecting a glycemic context 26 for a diagnostic test strip 5. For example, the adherence criteria can include criteria used in determining whether the indicated glycemic context 26 of the diagnostic test strip 5 closely enough adheres to expected glycemic context 26 of that diagnostic test strip 5 associated with a properly executed structured testing protocol 46. The adherence criteria in this example embodiment can be to check, for example, if the user insert the correct diagnostic test strip 5 into the test strip meter 14 with the glycemic context 26 associated with the scheduled test 48, or if the user completed all the scheduled tests 48 within a predetermined time period, or any other suitable adherence criteria. If the user does not adhere to the structured testing glycemic testing protocol 46, the user may be notified by the testing protocol advisor and/or test strip meter 14 and may be given the opportunity to test, or to re-test, depending on the adherence violation, using the correct diagnostic test strip 5 in a manner as described above for the non-structured testing protocol.

Further, the exit criteria can include criteria used to determine whether the structured testing protocol should end. In this example structured testing embodiment, the exit criterion may be, for example, that the user has successfully completed the structured testing glycemic testing protocol 46, that the user has not sufficiently adhered to the structured testing glycemic testing protocol 46 (i.e., a wrong diagnostic test strip 5 was used, a scheduled test 48 was missed), that the results of the scheduled test 48 are too high or too low for a predetermined number of times, or any other foreseeable exit criteria.

In another embodiment, a test strip meter 14 and a set of diagnostic test strips 5 with imprinted glycemic context codes 12 are provided to a user. In one embodiment, the diagnostic test strips 5 may be provided to a user in groups, pertaining to their encoded glycemic contexts 26 as described above. For example, each group of diagnostic test strips 5 may be configured to signal a different glycemic context 26. For example, the groups may include approximately 10 diagnostic test strips 5 having glycemic context codes 12 configured to signal a pre-prandial glycemic context 26; approximately 10 diagnostic test strips 5 configured to signal a post-prandial glycemic context 26; and approximately 10 diagnostic test strips 5 configured to signal a fasting glycemic contexts 26, etc. Other group sizes and groupings may also be provided, as will be appreciated by one of ordinary skill.

The user may select from the plurality of test strips 5, a diagnostic test strip 5 having a glycemic context code 12 appropriate to signal the proper glycemic context 26 pertaining to the user's glycemic state. As mentioned above, the glycemic context code 12 may be readily identified by the user by, for example, look or feel such that the glycemic context code 12 can suitably convey the glycemic context 26 associated with a particular diagnostic test strip 5 to the user. For example, a diagnostic test strip 5 having a glycemic context code 12 configured to signal a pre-prandial glycemic context 26 may have a glycemic context code 12 comprising a blue color strip. Each glycemic context 26 may have a distinct glycemic context code 12 so a user can quickly identify which diagnostic test strip 5 is configured to signal the appropriate glycemic context 26. The glycemic context code 12 may be selected from the group, including, but not limited to, a color code (not shown), a label 32 (FIG. 3), and combinations thereof. A context code identifier legend 40 may also be provider to the user.

In this embodiment, the user can simply be instructed to use the set of diagnostic test strips 5 as indicated by the glycemic context code 12 along with the test strip meter 14. Therefore, in this embodiment, a protocol advisor may not be needed. The user can simply be guided by the glycemic context code 12 itself. In other words, the user can be taught by the glycemic context code 12 under which conditions blood glucose tests should be taken. It also may be helpful to use a glycemic context code 12 which is readily identified to the user by, for example, look or feel, to quickly identify under which the conditions the blood glucose test should be taken. The taken blood glucose test can then be stored together with the glycemic context 26 either automatically, e.g., by being read by the test strip meter 14, or manually, e.g., via a data input by the user. Therefore, it may be possible to establish a testing protocol without having a protocol advisor. The data can then be evaluated and reported taking into account the established structured measurement procedure. Moreover, a testing protocol can be established by storing the information of the glycemic context code 12 and automatically generating a reminder system based on the stored information. For example, if it is determined that the user typically takes a blood glucose measurement within specific time windows and/or under specific conditions such that a pattern might be detected, an alarm can be generated if that specific time window and/or conditions are detected.

In one embodiment, the user can use the diagnostic test strip 5 marked with the fasting glycemic context code 12 after waking up, or after fasting for a predetermined amount of time; the diagnostic test strip 5 marked with the pre-prandial glycemic context code 12 before every meal; and the diagnostic test strip 5 marked with the post-prandial glycemic context code 12 after a predetermined time after every meal. In one embodiment, after a predetermined amount of time, the user and health care provider can review the blood glucose measurement results, as they are typically stored in the test strip meter 14. If the user correctly adheres to using the right diagnostic test strip 5 with the right associated glycemic context 26 of the event, e.g., fasting or meals, the user can create simply and cheaply a structured test protocol by reviewing these blood glucose values.

For the purposes of describing and defining the present invention, it is noted that reference herein to a variable being a "function" of a parameter or another variable is not intended to denote that the variable is exclusively a function of the listed parameter or variable. Rather, reference herein to a variable that is a "function" of a listed parameter is intended to be open ended such that the variable may be a function of a single parameter or a plurality of parameters.

It is also noted that recitations herein of "at least one" component, element, etc., should not be used to create an inference that the alternative use of the articles "a" or "an" should be limited to a single component, element, etc.

It is noted that recitations herein of a component of the present disclosure being "programmed" in a particular way, "configured" or "programmed" to embody a particular property, or function in a particular manner, are structural recitations, as opposed to recitations of intended use. More specifically, the references herein to the manner in which a component is "programmed" or "configured" denotes an existing physical condition of the component and, as such, is to be taken as a definite recitation of the structural characteristics of the component.

It is noted that terms like "preferably," "commonly," and "typically," when utilized herein, are not utilized to limit the scope of the claimed invention or to imply that certain features are critical, essential, or even important to the structure or function of the claimed invention. Rather, these terms are merely intended to identify particular aspects of an embodiment of the present disclosure or to emphasize alternative or additional features that may or may not be utilized in a particular embodiment of the present disclosure.

For the purposes of describing and defining the present invention it is noted that the terms "substantially" and "approximately" are utilized herein to represent the inherent degree of uncertainty that may be attributed to any quantitative comparison, value, measurement, or other representation. The terms "substantially" and "approximately" are also utilized herein to represent the degree by which a quantitative representation may vary from a stated reference without resulting in a change in the basic function of the subject matter at issue.

Having described the subject matter of the present disclosure in detail and by reference to specific embodiments thereof, it is noted that the various details disclosed herein should not be taken to imply that these details relate to elements that are essential components of the various embodiments described herein, even in cases where a particular element is illustrated in each of the drawings that accompany the present description. Rather, the claims appended hereto should be taken as the sole representation of the breadth of the present disclosure and the corresponding scope of the various inventions described herein. Further, it will be apparent that modifications and variations are possible without departing from the scope of the invention defined in the appended claims. More specifically, although some aspects of the present disclosure are identified herein as preferred or particularly advantageous, it is contemplated that the present disclosure is not necessarily limited to these aspects.

It is noted that one or more of the following claims utilize the term "wherein" as a transitional phrase. For the purposes of defining the present invention, it is noted that this term is introduced in the claims as an open-ended transitional phrase that is used to introduce a recitation of a series of characteristics of the structure and should be interpreted in like manner as the more commonly used open-ended preamble term "comprising."

What is claimed is:

1. A diagnostic test strip for assaying blood, the diagnostic test strip comprising:
a support element;
a glucose reagent, which reacts with glucose in the blood, provided on the support element; and
a glycemic context code provided on the support element, wherein the glycemic context code indicates a glycemic context for the diagnostic test strip.

2. The diagnostic test strip of claim 1, wherein the glycemic context code indicates the glycemic context of the diagnostic test strip to a test strip meter.

3. The diagnostic test strip of claim 2, wherein the glycemic context code is an optical signaling indicia, a mechanical signaling indicia, or combinations thereof.

4. The diagnostic test strip of claim 1, wherein the glycemic context code is machine-readable.

5. The diagnostic test strip of claim 4, wherein the glycemic context code indicates a glycemic context to a test strip meter upon insertion of the diagnostic test strip into the test strip meter.

6. The diagnostic test strip of claim 4, wherein the machine-readable glycemic context code is an optical signaling indicia, an electrical signaling indicia, a mechanical signaling indicia, or combinations thereof.

7. The diagnostic test strip of claim 6, wherein the optical signaling indicia is a bar code, a hole pattern, a color, or combinations thereof.

8. The diagnostic test strip of claim 6, wherein the mechanical signaling indicia is an indent pattern, a hole pattern, strip width or combinations thereof.

9. The diagnostic test strip of claim 6, wherein the electrical signal indicia is a resistance pattern, capacitance pattern, break pattern, or combinations thereof.

10. The diagnostic test strip of claim 1, wherein the glycemic context sets the condition under which a measurement of the blood is taken as pre-prandial, post-prandial, pre-event, post-event, fasting, bedtime, or combinations thereof.

11. A guided structured testing kit for assaying blood comprising a test strip container, a test strip meter, a testing protocol advisor, and at least one diagnostic test strip,
wherein the at least one diagnostic test strip comprises a support element, a reagent which reacts with glucose in the blood provided on the support element, and a glycemic context code provided on the support element, wherein the glycemic context code provides a glycemic context of the at least one diagnostic test strip,
wherein the test strip container defines an internal volume to hold the at least one diagnostic test strip, and
wherein the testing protocol advisor notifies a user of an at least one glycemic testing protocol and is provided in the testing kit as a paper tool, on the testing kit as a paper tool, in the testing kit as a stand-alone electronic device or electronically by the test strip meter.

12. The guided structured testing kit of claim 11, wherein the test strip meter comprises a memory system configured to store the glycemic context of the at least one diagnostic test strip when inputted into the test strip meter, and associate the inputted glycemic context with a blood glucose test result provided by the at least one diagnostic test strip.

13. The guided structured testing kit of claim 11, wherein the test strip container of the guided structured testing kit further comprises a lid, wherein the lid comprises at least one display, wherein the at least one display provides a visual notification of the at least one glycemic testing protocol.

14. The guided structured testing kit of claim 13, wherein the visual notification comprises a calendar comprising a plurality of scheduled tests.

15. The guided structured testing kit of claim 11, wherein the at least one glycemic testing protocol comprises at least one scheduled glycemic test.

16. The guided structured testing kit of claim 15, wherein the testing protocol advisor detects the status of the at least one of scheduled glycemic test.

17. The guided structured testing kit of claim 16, wherein the testing protocol advisor comprises a device to inform a user of a recommended action based on the status of the at least one scheduled glycemic test.

18. The guided structured testing kit of claim 11, wherein the glycemic testing protocol is programmable by a user.

19. The guided structured testing kit of claim 11, wherein the at least one diagnostic test strip comprises a glycemic context identifier corresponding to the indicated glycemic context of the at least one diagnostic test strip.

20. A method for performing a guided structured test for assaying blood, the method comprising:
providing a diagnostic test strip having a glycemic context code and a glucose reagent which reacts with glucose in blood associated with the diagnostic test strip and a test strip meter; applying blood to the diagnostic test strip;
executing a blood glucose measurement on the blood by inserting the diagnostic test strip into the test strip meter; and
signaling a glycemic context to the test strip meter by inputting the glycemic context code associated with the diagnostic test strip into the test strip meter, wherein the test strip meter associates the signaled glycemic context with a blood glucose test result provided by the diagnostic test strip and stores the blood glucose test result with the glycemic context in a memory of the test strip meter.

21. The method of claim 20, further comprising,
evaluating the blood glucose test result in conjugation with the glycemic context associated with that blood glucose test result.

22. The method of claim 20, further comprising,
generating a report with respect to the blood glucose test result and the glycemic context associated with that blood glucose test result.

23. The method of claim 20, further comprising,
establishing a reminder system based on historically stored glycemic context from the memory of the test strip meter which reminds a user to execute a blood glucose measurement within a specific time window and/or under specific conditions that have been determined from the historically stored glycemic context.

24. The method of claim 20, wherein the glycemic context is pre-prandial, post-prandial, pre-event, post-event, fasting, bedtime, or combinations thereof.

25. The method of claim 20, wherein the glycemic context code is machine-readable.

26. The method of claim 25, wherein the machine-readable glycemic context code is an optical signaling indicia, an electrical signaling indicia, a mechanical signaling indicia, or combinations thereof.

27. The method of claim 20, wherein a plausibility check is executed automatically by the test strip meter with respect to the glycemic context inputted via the glycemic context code and a signal is provided by the test strip meter if an incorrect glycemic context is provided.

28. The method of claim 27, wherein the plausibility check is based on a time, a current measured blood glucose value, historical data or combinations thereof.

29. The method of claim 20, wherein a signal is provided if a scheduled test is missed.

30. The method of claim 29, wherein the scheduled test is determined to be missed based on information about a time, a current measured blood glucose value, historical data or combinations thereof.

31. A guided structured testing kit for assaying blood comprising a test strip container, a test strip meter, a testing protocol advisor, and at least one diagnostic test strip, wherein the at least one diagnostic test strip comprises a support element, a reagent which reacts with glucose in the blood provided on the support element, and a glycemic context code provided on the support element, wherein the glycemic context code provides a glycemic context of the at least one diagnostic test strip,
wherein the test strip container defines at least one internal volume to hold the at least one diagnostic test strip and comprises a lid,
wherein the testing protocol advisor notifies a user of an at least one glycemic testing protocol, and is provided in the testing kit as a paper tool, on the testing kit as a paper tool, in the testing kit as a stand-alone electronic device or electronically by the test strip meter, and
wherein the lid comprises at least one display, wherein the at least one display provides a visual notification of the at least one glycemic testing protocol comprising a plurality of scheduled tests.

32. The guided structured testing kit of claim 31, wherein the testing protocol advisor is programmed with structured testing parameters.

33. A test strip container, the test strip container comprising:
at least one internal volume to hold at least one diagnostic test strip;
a plurality of a compartments, wherein each compartment houses at least one diagnostic test strip, wherein each diagnostic test strip comprises,
a support element,
a glucose reagent, which reacts with glucose in blood, provided on the support element, and
at least one glycemic context code provided on the test strip container and associated with each compartment in the plurality, wherein the glycemic context code indicates a glycemic context for the diagnostic test strip housed within each compartment.

* * * * *